United States Patent [19]

Venin et al.

[11] 4,352,351
[45] Oct. 5, 1982

[54] ELECTRONARCOSIS APPARATUS

[76] Inventors: Igor V. Venin, ulitsa Pozharskogo, 2, korpus 1, kv. 9; Tatyana V Vidershain, ulitsa Valovaya, 19, kv. 6; Vladimir I. Rodionov, ulitsa Zayachkivskogo, 7, kv. 27; Andrei A. Smerdov, ulitsa Tudora, 14, kv. 6, all of Lvov; Viktor Y. Tabak, ulitsa Vyshnyakovskaya, 33, kv. 115, Moscow, all of U.S.S.R.

[21] Appl. No.: 190,329

[22] Filed: Sep. 24, 1980

[30] Foreign Application Priority Data

Jan. 25, 1978 [SU] U.S.S.R. .............................. 2573685

[51] Int. Cl.³ .............................................. A61N 1/34
[52] U.S. Cl. .................................. 128/1 C; 128/419 D
[58] Field of Search ........................... 128/1 C, 419 D

[56] References Cited

U.S. PATENT DOCUMENTS

| | | | |
|---|---|---|---|
| 3,236,239 | 2/1966 | Berkovits | 128/419 D |
| 3,626,926 | 12/1971 | Kuzin et al. | 128/1 C |
| 3,791,373 | 2/1974 | Winkler et al. | 128/1 C |
| 3,989,051 | 11/1976 | Nozhnikov et al. | 128/1 C |
| 4,114,628 | 9/1978 | Rizk | 128/419 D |

Primary Examiner—William E. Kamm
Attorney, Agent, or Firm—Steinberg & Raskin

[57] ABSTRACT

Each of two channels has a sine wave oscillator, an electronic key, an amplifier and a pair of electrodes, electrically connected in series. A pair of threshold circuits are provided. Each of the threshold circuits has an input electrically connected to the amplifier of a corresponding one of the channels and an output. A first coincidence circuit has a pair of inputs each electrically connected to the output of a corresponding one of the threshold circuits, and an output. The output of the first coincidence circuit is electrically connected to a first input of a second coincidence circuit. The second coincidence circuit has a second input to which signals are fed from the output of a first time delay element. The output of the first time delay element is also connected to the input of a second time delay element. The output of the second time delay element is electrically connected to the control inputs of the electronic keys of the channels. The output signal of the second coincidence circuit is used to trigger defibrillator synchronization.

1 Claim, 1 Drawing Figure

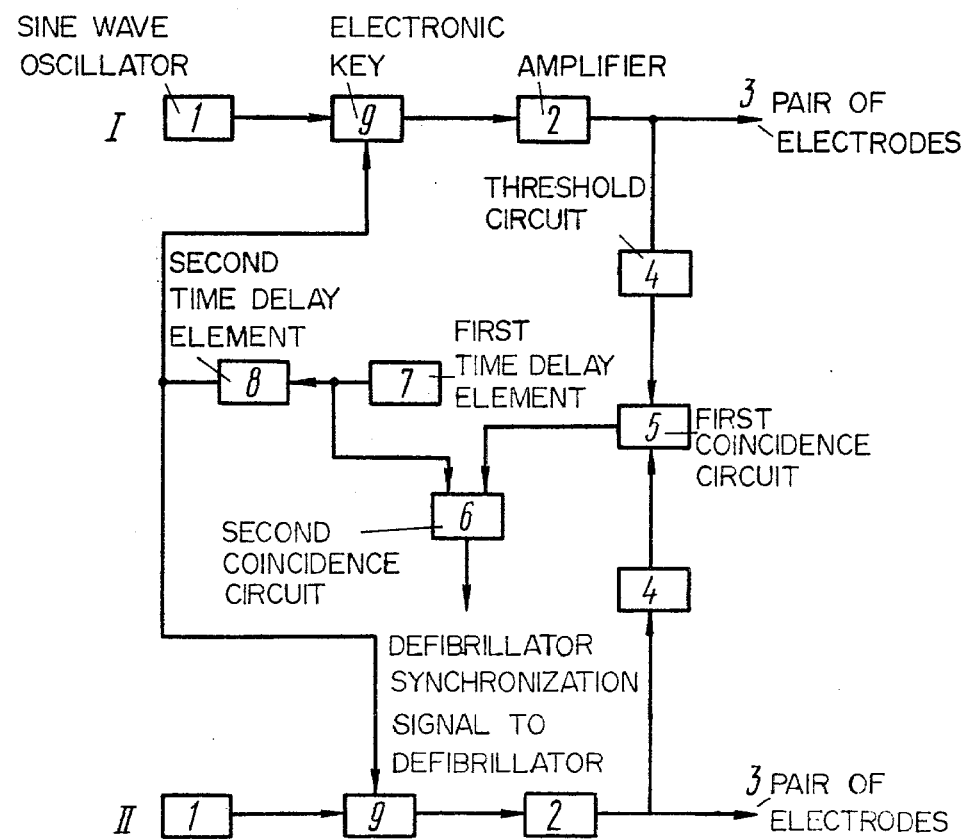

ELECTRONARCOSIS APPARATUS

BACKGROUND OF THE INVENTION

The present invention relates to medical engineering. More particularly, the invention relates to general anesthesia, and especially to apparatus for electronarcosis.

The apparatus of the invention may find application for transitory general anesthesia in electroimpulse heart defibrillation, for example.

An embodiment of electronarcosis apparatus of the prior art is known to include two identical electric channels, each comprising a sine wave oscillator, an amplifier and a pair of electrodes arranged on the patient's head. These components are electrically connected in series. The apparatus is provided with a regulator to control the current in the electrode circuit, and pointer instruments to measure the currents. The apparatus also comprises a circuit commutator for switching the outputs of the amplifiers over from the electrodes to the equivalent load. Thus, each of the channels can be checked for serviceability prior to applying electronarcosis (cf. U.S. Pat. No. 3,626,926).

The aforedescribed known apparatus is adapted to conduct a session of electronarcosis during which the physician can regulate the intensity of the current in each of the channels, proceeding from the condition of the patient, as judged against respective criteria. This assures a required depth of penetration of the anesthetic effect, while taking into account an individual reaction of the patient to the effect of electronarcosis. Further, the operator is in a position to gradually increase the intensity of the current in both channels at a slow rate, in the course of a lengthy application of electronarcosis, particularly in order to compensate for the "habituation" of the patient to the effect of electronarcosis. When there is a lengthy session of electronarcosis, as is the case in various surgical interventions, the intensity of the currents in the channels required to apply anesthesia to the patient operated upon, may vary substantially from the beginning to the end of the session.

Whenever the patient is exposed to a transient therapeutic effect accompanied by excessively painful sensations, for example, in electrical defibrillation of the heart, short-time application of electronarcosis is required.

In particular, the peculiarities of the defibrillation method under electronarcosis involve feeding of the electronarcosis current to the patient's circuit "jumpwise", a few tenths of a second before beginning defibrillation of the heart, and instantaneous termination of the current supply just after relieving the defibrillation effect.

The known electronarcosis apparatus is applicable for transitory anesthesia of the patient in electric heart defibrillation.

Since the anesthetic effect is a transitory one and current intensity regulation is rendered impossible in the course of the process, the effective dose is set in the known apparatus using a device for preoperational testing of the apparatus, by adjusting the current in each of the channels against an equivalent load prior to beginning electronarcosis treatment.

To accomplish this, the outputs of the amplifiers are changed, by the circuit commutator, to the equivalent load and the current intensity required for a general anesthesia of the patient is set by the current regulator. Thereafter, current feed is terminated and the outputs of the apparatus are connected to electrodes appropriately arranged on the patient's head. The defibrillator electrodes are placed on the patient's breast and the defibrillator is prepared for operation. That is, the capacitor is charged. The electronarcosis current feed is then instituted and the operator, after making sure that the current intensity in the circuit of each channel corresponds to preset values as against the pointer indicators, applies the defibrillation effect to the patient without interrupting the application of electronarcosis. The electronarcosis effect is thereafter terminated.

However, since the resistance of the equivalent load is not equal to the resistance offered by the patient's biological tissues across the electrodes, use of the preoperational testing device for presetting a required current intensity against the equivalent load might result in the differing of the actual intensity of the currents applied to the patient from those preset against the equivalent load.

Any excess of the preset intensity of currents applied to the patient entails a danger of inflicting an electric shock on the patient. The application of too low a current entails a danger of defibrillation without anesthesia, or with an inadequately deep anesthesia, which could cause pain shock in the patient.

Only manual control over the anesthetic and defibrillation effects may be carried out by the operator while applying defibrillation under anesthesia, utilizing the known apparatus. The electronarcosis application time before and after the defibrillation effect is therefore set by the operator. This may create a source of error, especially under strenuous conditions of rendering prompt aid to a patient in critical condition. Thus, an overshortened electroanesthesia application time, as well as an erroneous sequence of application of defibrillation and electronarcosis, that is, defibrillation being either preceded or followed by the application of electronarcosis, may aggravate the condition of the patient.

SUMMARY OF THE INVENTION

The principal object of the invention is to provide electronarcosis apparatus which produces a transitory electronarcosis effect with great safety.

An object of the invention is to provide electronarcosis apparatus which produces an electronarcosis effect of less than a few tenths of a second with great safety.

Another object of the invention is to provide electronarcosis apparatus which functions efficiently, effectively, reliably and with great safety to the patient to produce a transitory electronarcosis effect.

Still another object of the invention is to provide electronarcosis apparatus which automatically maintains a sequence of application of an electronarcosis effect and a defibrillator discharge to a patient under treatment in a manner whereby the effective time of electronarcosis applied before and after delivery of a defibrillation pulse is controlled automatically.

Yet another object of the invention is to provide electronarcosis apparatus which interlocks the defibrillator operation in case of current deviation from a preset value in either of the channels, thereby preventing the possibility of application of a defibrillation effect to a patient with an inadequate electronarcosis.

These objects are accomplished by the electronarcosis apparatus of the invention, which comprises two channels each having a sine wave oscillator, an amplifier and a pair of electrodes, electrically connected in series. A pair of threshold circuits are provided. Each of the threshold circuits has an input electrically connected to the output of the amplifier of a corresponding one of the channels and an output. A first coincidence circuit has a pair of inputs each electrically connected to the output of a corresponding one of the threshold circuits, and an output. The output of the first coincidence circuit is electrically connected to a first input of a second coincidence circuit. The second coincidence circuit has a second input to which signals are fed from the output of a first time delay element. The output of the first time delay element is also connected to the input of a second time delay element. The output of the second time delay element is electrically connected to the control inputs of electronic keys electrically connected in series in the channels.

The electronarcosis apparatus of the present invention is capable of automatically maintaining a strict sequence of application of an electronarcosis effect and a defibrillator discharge to a patient under treatment, in such a manner that the effective time of electronarcosis applied before and after delivery of a defibrillation pulse is controlled automatically. The apparatus of the invention also provides for interlocking of the defibrillator operation in case of current deviation from a preset value in either of the channels, thereby preventing the possibility of application of a defibrillation effect to a patient with an inadequate electronarcosis.

BRIEF DESCRIPTION OF THE DRAWINGS

For a fuller understanding of the invention, reference is had to the following description, taken in connection with the accompanying drawing, in which the single FIGURE is a block diagram of an embodiment of the electronarcosis apparatus of the invention.

DESCRIPTION OF THE PREFERRED EMBODIMENTS

The electronarcosis apparatus of the invention comprises two channels I, II, each including a sine wave oscillator 1, an amplifier 2 and a pair of electrodes 3, electrically connected in series. In accordance with the invention, a pair of threshold circuits 4 are provided. Each of the threshold circuits 4 has an input electrically connected to the output of the amplifier 2 of a corresponding one of the channels I and II. The threshold circuits 4 may consist, in particular, of electronic voltage comparators. Whenever necessary, appropriate matching devices (not shown in the FIGURE) may be electrically connected between the inputs of the threshold circuits or voltage comparators 4 and the outputs of the amplifiers 2. The matching elements and the threshold circuits 4 must provide a signal appearing at the outputs of said threshold circuits if the currents in the circuits of the electrodes 3 correspond to preset values.

In the apparatus of the invention, the value of the signal at the outputs of the sine wave oscillators 1 and the gain factor of the amplifiers 2 are chosen to insure in the circuit of each pair of electrodes 3 a current value necessary to achieve general anesthesia of the patient, more particularly, 170 to 180 mA (cf. Resuscitation, 3, 1974, pp. 223–227, V. A. Negovsky et al, "Short-Term Electronarcosis: A New Method Of General Anesthesia For Defibrillation"). The threshold circuits 4 monitor the current value in the circuit of each pair of electrodes 3 and produce a signal at the outputs thereof when the current in the circuit of said electrodes corresponds to a preset value. Such value is that at which general anesthesia of the patient is attained and, consequently, defibrillation can be conducted. When the threshold circuits 4 consist of electronic voltage comparators, one of the comparator inputs is coupled to the output of amplifier 2 via respective matching devices. A reference voltage, having a scale which corresponds to the preset value of the current in the circuit of the electrodes 3, is applied to the second input of the comparator from a respective source.

The outputs of the threshold circuits 4 are electrically connected to respective inputs of a first coincidence circuit 5. The output of the first coincidence circuit 5 is electrically connected to a first input of a second coincidence circuit 6. The coincidence circuit 7 is connected to the start button 10. The second input of the second coincidence circuit 6 is electrically connected to the output of a first time delay element 7. The delay time established by the first time delay element 7 corresponds to the time of application of electronarcosis before the delivery of a defibrillation pulse. Matching of the inputs of the second coincidence circuit 6 with the outputs of the first coincidence circuit 5 and the first time delay element 7 must insure the appearance of a signal at the output of said second coincidence circuit if there is a signal at the output of said first coincidence circuit, as well as signal corresponding to the end of the time interval defined by said first time delay element.

A signal from the output of the second coincidence circuit 6 may be used for defibrillator synchronization. More particularly, use may be made of the defibrillator input adapted for synchronizing the defibrillation effect with the bioelectric signal of the patient's heart. If necessary, additional matching devices may be electrically connected between the output of the second coincidence circuit 6 and the synchronizing input of the defibrillator (not shown) in the FIGURE), corresponding to the type of defibrillator used.

The output of the first time delay element 7 is also electrically connected to the input of a second time delay element 8. The output of the second time delay element 8 is electrically connected to the control inputs of the electronic keys 9 of the channels I and II. The second time delay element 8 provides a time interval corresponding to the duration of the time of application of the electronarcosis, following the delivery of the defibrillation pulse. The control inputs of the electronic keys 9 are matched with the output of the second time delay element 8 in such a manner that a signal appearing at said output and corresponding to the end of the time delay interval, should open said keys.

The electronarcosis apparatus of the present invention operates as follows. The output of the second coincidence circuit 6 must be connected to the defibrillator synchronization input. The two pairs of electrodes 3 are placed on the patient's head (not shown in the FIGURE) The electronarcosis current regulator is set to a position corresponding to a required current intensity, with the result that the defibrillator is charged to an appropriate level and is changed for synchronized operation. The defibrillator electrodes are arranged in an appropriate manner on the thoracic cage of the patient. The operator must then push the defibrillator start button, whereby the defibrillator will operate in response to a corresponding signal arriving at its synchronizing input. The operator must then push the start button 10 of the electronarcosis apparatus in order to open the electronic keys 9 and trigger the first time delay element 7. A sine wave voltage from the output of the oscillator 1 then passes along both of the channels I and II to be applied to the amplifiers 2 via the electronic keys 9, whereby currents start flowing in the circuit of the two pairs of electrodes 3. These currents, while acting upon the inputs of the threshold circuits 4, cause said threshold circuits to operate provided the current in the corresponding channel I or II is of a preset value. Should such be the case, signals appear at the outputs of both threshold circuits 4. If signals are applied to both inputs of the first coincidence circuit 5, a signal appears at its output. Such signal is then applied to the first input of the second coincidence circuit 6. Thus, such a signal may appear if the currents in the circuits of both pairs of electrodes 3 have preset values.

A signal from the first time delay element 7 is delivered to the second input of the second coincidence circuit 6. The first time delay element 7 defines a time interval corresponding to the effective application time of electronarcosis from the instant of pushing the start button 10 to the delivery of a defibrillation pulse. Upon the lapse of this time interval, the defibrillator may be discharged, provided that the currents in the circuits of both pairs of electrodes 3 of both channels I and II correspond to preset values. This occurs in response to signals arriving at both inputs of the second coincidence circuit 6; one from the first coincidence circuit 5 and the other from the first time delay element 7. If such is the case, a signal appears at the output of the second coincidence circuit 6. The signal is then delivered to the defibrillator synchronizing input to actuate the defibrillator, whereby a defibrillation pulse is applied to the patient's thoracic cage.

The signal from the output of the first time delay element 7 is also fed to the input of the second time delay element 8, which defines a time interval corresponding to the duration of the defibrillation pulse and the effective time of electronarcosis from the delivery of the defibrillation pulse to the end of the treatment procedure. Upon the lapse of such period of time a signal from the output of the second time, delay element 8 is fed to the control inputs of the electronic keys 9 to open said keys. This opens the supply circuits of the sine wave voltage from the oscillators 1 to the inputs of the amplifiers 2, and the circuits of the electrodes 3 of both channels I and II are deenergized. If it is necessary to repeat the electrical defibrillation with short-term electronarcosis, the defibrillator must again be prepared for operation and the electronarcosis apparatus must again be started. That is, the keys 9 must be closed and the first time delay element 7 must be triggered.

Whenever the current in either of the electronarcosis channels I and II is found to have deviated from a preset value for a period of time, defined by the time delay element 7, no signal will appear at the output of the respective threshold circuit 4 nor will any signal appear at the output of the first coincidence circuit 5. In such a case, a signal appearing at the second input of the second coincidence circuit 6 from the first time delay element 7 will not actuate the defibrillator. This prevents the possibility of the application of a defibrillation pulse to the patient if any of the electrodes 3 is out of order.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Electronarcosis apparatus, comprising first and second channels each having a sine wave oscillator having an output, an electronic key electrically connected to the output of said oscillator and having a control input and an output, an amplifier electrically connected to the output of said key and having an output, and a pair of electrodes electrically connected to the output of said amplifier;

a first threshold circuit having an input electrically connected to the output of the amplifier of said first channel and an output;

a second threshold circuit having an input electrically connected to the output of the amplifier of said second channel and an output;

a first coincidence circuit having a first input electrically connected to the output of said first threshold circuit, a second input electrically connected to the output of said second threshold circuit and an output;

a second coincidence circuit having a first input electrically connected to the output of said first coincidence circuit, a second input and an output;

a first time delay element having an output electrically connected to the second input of said second coincidence circuit; and a second time delay element having an input electrically connected to the output of said first time delay element and an output electrically connected to the control inputs of said electronic keys, said second coincidence circuit providing at its output an output signal for triggering defibrillator synchronization.

* * * * *